United States Patent [19]

Willcocks

[11] Patent Number: 4,640,928

[45] Date of Patent: Feb. 3, 1987

[54] 4-(2-HYDROXY-1-PYRROLIDINYL AND 1-PIPERIDINYL)-2H-BENZO[B]-PYRAN-3-OL DERIVATIVES

[75] Inventor: Kenneth Willcocks, Old Harlow, England

[73] Assignee: Beecham Group p.l.c., England

[21] Appl. No.: 782,508

[22] Filed: Oct. 1, 1985

Related U.S. Application Data

[63] Continuation-in-part of Ser. No. 489,248, Apr. 27, 1983, abandoned.

[30] Foreign Application Priority Data

Apr. 28, 1982 [GB] United Kingdom ................. 8212359
Sep. 15, 1982 [ZM] Zambia ................................. 76/82
Sep. 21, 1982 [GB] United Kingdom ................. 8226914

[51] Int. Cl.[4] .................... C07D 405/04; A61K 31/35
[52] U.S. Cl. .................... 514/422; 514/320; 546/196; 548/525
[58] Field of Search .................... 546/196; 548/525; 514/320, 422

[56] References Cited

U.S. PATENT DOCUMENTS 4,446,113  5/1984  Evans et al. .................... 548/525 X

FOREIGN PATENT DOCUMENTS 46652  3/1982  European Pat. Off. ........ 544/399 X

Primary Examiner—Donald G. Daus
Assistant Examiner—William A. Teoli, Jr.
Attorney, Agent, or Firm—Jacobs & Jacobs

[57] ABSTRACT

Compounds of formula (I):

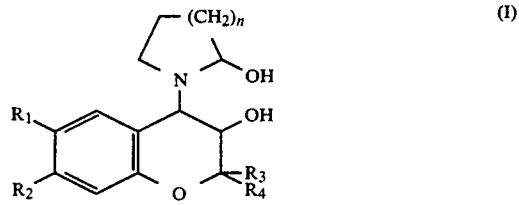

wherein:
either one of $R_1$ and $R_2$ is hydrogen and the other is selected from the class of $C_{1-6}$ alkylcarbonyl, benzoyl, $C_{1-6}$ alkoxycarbonyl, $C_{1-6}$ alkylcarbonyloxy, $C_{1-6}$ alkylhydroxymethyl, nitro, cyano, chloro, trifluoromethyl, $C_{1-6}$ alkylsulphinyl, $C_{1-6}$ alkylsulphonyl, $C_{1-6}$ alkoxysulphinyl, $C_{1-6}$ alkoxysulphonyl, $C_{1-6}$ alkylcarbonylamino, $C_{1-6}$ alkoxycarbonylamino, $C_{1-6}$ alkylthiocarbonyl, $C_{1-6}$ alkoxy-thiocarbonyl, $C_{1-6}$ alkylthiocarbonyloxy, $C_{1-6}$ alkyl-thiolmethyl, formyl or aminosulphinyl, aminosulphonyl or aminocarbonyl, the amino moiety being optionally substituted by one or two $C_{1-6}$ alkyl groups, or $C_{1-6}$ alkylsulphinylamino, $C_{1-6}$ alkylsulphonylamino $C_{1-6}$ alkoxysulphinylamino or $C_{1-6}$ alkoxysulphonylamino or ethylenyl terminally substituted by $C_{1-6}$ alkylcarbonyl, nitro or cyano, or —C($C_{1-6}$ alkyl)NOH or —C($C_{1-6}$ alkyl)NNH$_2$, or one of $R_1$ and $R_2$ is nitro, cyano or $C_{1-3}$ alkylcarbonyl and the other is methoxy or amino optionally substituted by one or two $C_{1-6}$ alkyl or by $C_{2-7}$ alkanoyl;
one of $R_3$ and $R_4$ is hydrogen or $C_{1-4}$ alkyl and the other is $C_{1-4}$ alkyl or $R_3$ and $R_4$ together are $C_{2-5}$ polymethylene having anti-hypertensive activity.

8 Claims, No Drawings

4-(2-HYDROXY-1-PYRROLIDINYL AND 1-PIPERIDINYL)-2H-BENZO[B]-PYRAN-3-OL DERIVATIVES

The present application is a continuation-in-part of my copending application, Ser. No. 489,248, filed Apr. 27, 1983 now abandoned.

The present invention relates to novel chromanols having pharmacological activity, to a process for preparing them, to pharmaceutical compositions containing them, and to their use in the treatment of mammals.

The novel chromanols of my invention are also useful as intermediates to make the benzopyrans of U.S. Pat. No. 4,446,113 issued May 1, 1984, as shown, for example, in Example 3 hereof.

U.S. Pat. No. 4,110,347 discloses compounds having blood pressure lowering activity which are of formula (A'):

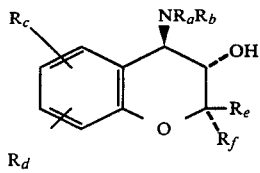

and acid addition salts thereof wherein $R_a$ is a hydrogen atom or a $C_{1-9}$ hydrocarbon group optionally substituted by a hydroxyl or $C_{1-6}$ alkoxyl group; $R_b$ is a hydrogen atom or $C_{1-6}$ alkyl group, or $NR_aR_b$ is a 3-8 membered heterocyclic group optionally substituted by one or two methyl groups; $R_c$ is a hydrogen or halogen atom or a $C_{1-6}$ alkyl, $C_{2-6}$ alkenyl, $C_{1-6}$ alkoxy, $C_{2-6}$ alkenoxyl, $C_{1-6}$ alkylthio, hydroxyl, amino, $C_{1-6}$ alkylamino, $C_{1-6}$ dialkylamino, nitro, trifluoromethyl, $C_{2-7}$ acylamino, $C_{1-6}$ alkoxysulphonylamino, carboxyl, nitrole or $AOR_g$, $ASR_g$, $ASO_2R_g$, $ANHR_g$, $ANR_gCOR_h$, $ANR_gSO_2R_h$ or $ANR_gCO_2R_h$ group, in which A is an alkylene group of 1-4 carbon, $R_g$ is an alkyl group of 1-4 carbon atoms, and $R_h$ is an alkyl group of 1 to 4 carbon atoms; and $R_d$ is a hydrogen or halogen atom or methyl or methoxy, or $R_c$ together with $R_d$ forms a —CH=CH—CH=CH—, —NH—CH=CH—, —CH$_2$—CH$_2$—CH$_2$—CH$_2$— or —CH$_2$—CH$_2$—CH$_2$—CO— system; $R_e$ is a hydrogen atom or a $C_{1-6}$ alkyl or phenyl group; and $R_f$ is a hydrogen atom or a $C_{1-6}$ alkyl or phenyl group.

U.S. Pat. No. 4,251,537 discloses compounds having useful anti-hypertensive activity, which are of formula (B'):

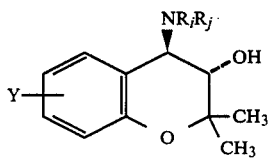

wherein $R_i$ is a hydrogen atom or an alkyl group of up to 4 carbon atoms optionally substituted by a chlorine or bromine atom or by a hydroxyl group or by an alkoxyl group of up to 4 carbon atoms or by an acyloxy group of up to 4 carbon atoms and $R_j$ is a hydrogen atom or an alkyl group of up to 4 carbon atoms or $R_i$ is joined to $R_j$ so that together with the nitrogen atom to which they are attached they form a 5-, 6- or 7-membered heterocyclic ring which is optionally substituted by methyl; Y is a group $COR_k$, $CO_2R_k$, $SOR_k$, $SO_2R_k$, $SOOR_k$, $SO_2OR_k$, $CH(OH)R_k$, $C(R_k)$=NOH, $C(R_k)$=NNH$_2$, $CONH_2$, $CONR_1R_m$, $SONR_1R_m$ or $SO_2NR_1R_m$ where $R_k$ and $R_1$ are each independently a hydrocarbon group of up to 8 carbon atoms or such a group inertly substituted by a chlorine or bromine atom or by a hydroxyl group or by an alkoxyl group of 1–4 carbon atoms or by an acyloxy group of up to 4 carbon atoms or by 3 fluorine atoms attached to the same carbon atom and $R_m$ is a hydrogen atom or an alkyl group of up to 4 carbon atoms; and salts thereof and O-acyl derivatives thereof wherein the O-acyl moiety contains up to 18 carbon atoms.

European Patent Publication 9912 describes antihypertensive compounds of formula (C'):

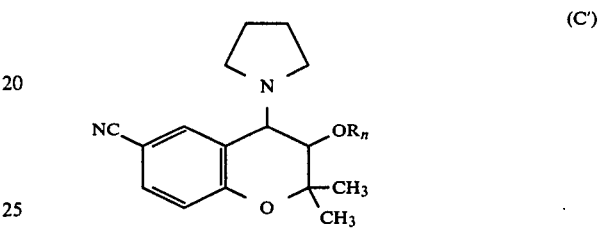

wherein the pyrrolidino and $OR_n$ moieties are trans and wherein $R_n$ is a hydrogen atom, an alkyl group of 1 to 3 carbon atoms or an acyl group of 1 to 8 carbon atoms; or a pharmaceutically acceptable acid addition salt thereof.

European Patent Publication 28449 describes compounds having blood pressure lowering activity, with low levels of unwanted cardiac effects, which compounds are of formula (D'):

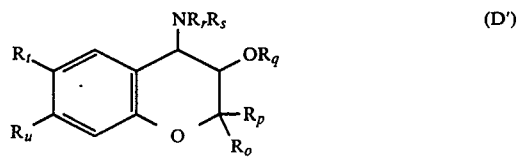

$R_o$ is a hydrogen atom or a lower alkyl group;
$R_p$ is a hydrogen atom or a lower alkyl group;
$R_q$ is a hydrogen atom or a lower alkyl group;
$R_r$ is a hydrogen atom or a lower alkyl group;
$R_s$ is a lower alkyl or a substituted alkyl group;
or $R_4$ and $R_5$ are joined so that together with the nitrogen atom to which they are attached they form a 5-, 6- or 7-membered ring optionally containing an oxygen or sulphur atom;
$R_t$ is an electron withdrawing group;
$R_u$ is an electron donating group; and the $NR_rR_s$ and $OR_q$ moieties are trans.

European patent publication 28064 describes compounds having blood pressure lowering activity, with low levels of unwanted cardiac effects, which compounds are of formula (E'):

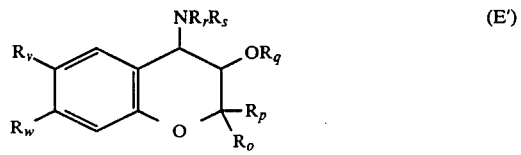

and salts and pro-drugs thereof, wherein: $R_o$ $R_p$ $R_q$ $R_r$ and $R_s$ are as defined for formula (D'), and $R_v$ is an electron donating group and $R_w$ is an electron withdrawing group; and the $NR_rR_s$ and $OR_q$ moieties are trans.

A class of chromanols have now been discovered and have been found to have blood pressure lowering activity.

Accordingly, the present invention provides a compound of formula (I):

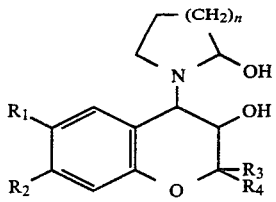
(I)

wherein:
either one of $R_1$ and $R_2$ is hydrogen and the other is selected from the class of $C_{1-6}$ alkylcarbonyl, benzoyl, $C_{1-6}$ alkoxycarbonyl, $C_{1-6}$ alkylcarbonyloxy, $C_{1-6}$ alkylhydroxymethyl, nitro, cyano, chloro, trifluoromethyl, $C_{1-6}$ alkylsulphinyl, $C_{1-6}$ alkylsulphonyl, $C_{1-6}$ alkoxysulphinyl, $C_{1-6}$ alkoxysulphonyl, $C_{1-6}$ alkylcarbonylamino, $C_{1-6}$ alkoxycarbonylamino, $C_{1-6}$ alkylthiocarbonyl, $C_{1-6}$ alkoxy-thiocarbonyl, $C_{1-6}$ alkylthiocarbonyloxy, $C_{1-6}$ alkyl-thiolmethyl, formyl or aminosulphinyl, aminosulphonyl or aminocarbonyl, the amino moiety being optionally substituted by one or two $C_{1-6}$ alkyl groups, or $C_{1-6}$ alkylsulphinylamino, $C_{1-6}$ alkylsulphonylamino $C_{1-6}$ alkoxysulphinylamino or $C_{1-6}$ alkoxysulphonylamino or ethylenyl terminally substituted by $C_{1-6}$ alkylcarbonyl, nitro or cyano, or —C($C_{1-6}$ alkyl)NOH or —C($C_{1-6}$ alkyl)NNH$_2$, or one of $R_1$ and $R_2$ is nitro, cyano or $C_{1-3}$ alkylcarbonyl and the other is methoxy or amino optionally substituted by one or two $C_{1-6}$ alkyl or by $C_{2-7}$ alkanoyl;
one of $R_3$ and $R_4$ is hydrogen or $C_{1-4}$ alkyl and the other is $C_{1-4}$ alkyl or $R_3$ and $R_4$ together are $C_{2-5}$ polymethylene;
the azacycle and OH moieties are trans; and
n is 1 or 2; or when one or other of $R_1$ and $R_2$ is an amino or an amino-containing group, a pharmaceutically acceptable salt thereof.

When one of $R_1$ and $R_2$ is hydrogen, the other is favourably selected from the class of $C_{1-6}$ alkylcarbonyl, $C_{1-6}$ alkoxycarbonyl, $C_{1-6}$ alkylcarbonyloxy, $C_{1-6}$ alkylhydroxymethyl, nitro cyano or chloro. In particular, when one of $R_1$ and $R_2$ is hydrogen, the other is preferably nitro or cyano.

When one of $R_1$ and $R_2$ is hydrogen, it is preferred that $R_2$ is hydrogen.

When one of $R_1$ and $R_2$ is nitro, cyano or $C_{1-3}$ alkylcarbonyl the other is preferably amino optionally substituted by one or two $C_{1-6}$ alkyl or by $C_{2-7}$ alkanoyl. In particular, when one of $R_1$ and $R_2$ is nitro, cyano or $C_{1-3}$ alkylcarbonyl, the other is amino, methylamino, dimethylamino or acetylamino. Most preferably, one of $R_1$ and $R_2$ is nitro or cyano and the other is amino.

When one of $R_1$ and $R_2$ is nitro, cyano or $C_{1-3}$ alkylcarbonyl, it is preferred that $R_1$ is nitro, cyano or $C_{1-3}$ alkylcarbonyl.

The alkyl groups or alkyl moieties of alkyl-containing groups for $R_1$ or $R_2$ are, preferably, methyl or ethyl.

Favourably, $R_3$ and $R_4$ are both alkyl having from 1 to 4 carbon atoms including methyl ethyl, n- and isopropyl. They are both methyl or ethyl, preferably both methyl.

It is preferred that the compounds of formula (I) are in substantially pure form.

There is a group of compounds within formula (I) wherein one of $R_1$ and $R_2$ is hydrogen and the other is selected from the class of $C_{1-6}$ alkoxycarbonyl, $C_{1-3}$ alkylhydroxymethyl, nitro or cyano, or one of $R_1$ and $R_2$ is nitro or cyano and the other is amino optionally substituted by one or two $C_{1-4}$ alkyl or by $C_{2-6}$ alkanoyl; $R_3$ is hydrogen or $C_{1-4}$ alkyl; $R_4$ is $C_{1-4}$ alkyl; and the remaining variables are as defined in formula (I).

It will be appreciated that there is a favourable sub-group of compounds within formula (I) of formula (II):

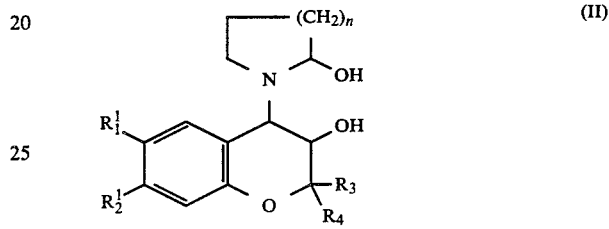
(II)

wherein one of $R_1^1$ and $R_2^1$ is hydrogen and the other is cyano or nitro and the remaining variable are as defined in formula (I).

Suitable and preferred values for the variables are as described under formula (I).

From the aforesaid it will be appreciated that there is a preferred compound within formula (II) of formula (III):

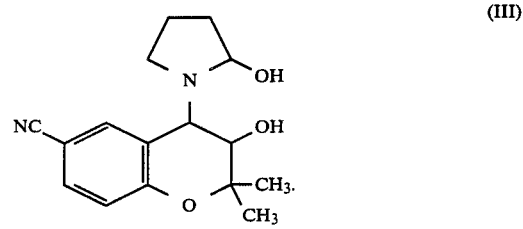
(III)

There is a further sub-group of compounds within formula (I) of formula (IV):

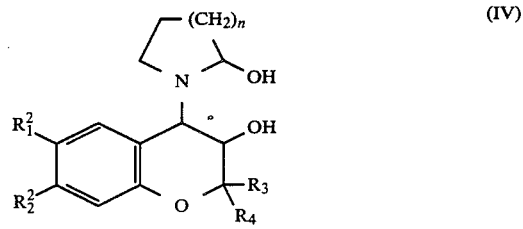
(IV)

wherein: one of $R_1^2$ and $R_2^2$ is cyano or nitro and the other is optionally substituted amino as defined and the remaining variables are as defined in formula (I).

Favourably $R_1^2$ is cyano or nitro and $R_2^2$ is amino. Suitable and preferred values for the remaining variablesare as described under formula (I).

The azacycle and OH are of course trans.

It will be appreciated that compounds of formula (I) have asymmetric centers, marked * in formula (I). The present invention extends to the isomers including entantiomers individually and the mixtures including racemates of these isomers.

It is particularly convenient to prepare and use the compounds of the formula (I) as isomeric mixtures. The isomers may be separated from another by conventional methods such as chromatography on a chiral phase or resolution using an optically active acid.

The present invention also provides a process for the preparation of a compound of the formula (I) or a pharmaceutically acceptable salt thereof which process comprises the cyclisation of the compound of the formula (V) or a salt thereof:

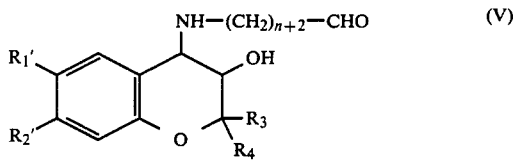

wherein $R_1'$ and $R_2'$ are $R_1$ and $R_2$ respectively or a group or atom convertible thereto; and thereafter optionally converting $R_1'$ or $R_2'$ to $R_1$ or $R_2$ respectively and, when one of $R_1$ and $R_2$ in the compound of formula (I) is an amino containing group, optionally forming a pharmaceutically acceptable salt thereof.

The cyclisation to form the azacycle in formula (I) may be effected under ambient conditions in protic e.g. aqueous medium preferably under conventional acid catalysis.

The trans isomer as defined in formula (I) is formed stereospecifically.

Examples of optional conversions of $R_1$ or $R_2$ in a compound of formula (I) into another $R_1$ or $R_2$, as defined hereinbefore, are generally known in the art of aromatic chemistry. For example, and α-hydroxyethyl group may be converted into acetyl by oxidation, a chloro atom may be converted into an amino group by amination, an amino group may be converted into amino substituted by one or two $C_{1-6}$ alkyl or by $C_{2-7}$ alkanoyl, or an hydrogen atom may be converted into a nitro group by nitration.

$R_1'$ or $R_2'$ may be protected amino, in which case examples of N-protecting groups include $C_{2-6}$ alkanoyl, for example acetyl, propionyl, and n-and iso-butryl and 2,2-dimethylpropanoyl, trifluoroacetyl; benzoyl optionally substituted in the phenyl ring by one or two substituents selected form $C_{1-4}$ alkyl, $C_{1-4}$ alkoxy, trifluoromethyl, halogen or nitro; $C_{1-4}$ for example tert-butoxycarbonyl; or benzyl optionally substituted as for benzyl above.

When $R_1'$ or $R_2'$ is amino protected by optionally substituted benzoyl, or $C_{2-7}$ alkanoyl, conversion is effected by conventional hydrolysis. $R_1'$, $R_2$ $C_{1-4}$ alkanoyl may be converted to $R_1'$, $R_2$ $C_{1-4}$ alkyl by conventional reduction.

When $R_1/R_2$ is $C_{1-6}$ alkoxycarbonyl or is optionally substituted benzyl, conversion to hydrogen may be carried out conventionally, for example by hydrogenolysis; this is conveniently effected by conventional methods such as transition metal catalysed hydrogenolysis, using for example palladium or platinum-charcoal, at about atmospheric pressure. Non-extreme temperatures at about ambient are generally suitable.

The resulting amino group hydrogen is conveniently converted to $C_{1-6}$ alkyl by reductive acylation for example by reaction of the compound of the formula (I) with the corresponding $C_{1-6}$ alkanoic acid in the presence of an conventional inorganic reductant such as iron/acetic acid/acetic anhydride.

Conversion to methyl may be effected with formaldehyde in the presence of a mild reductant such as sodium cyanoborohydride in an inert highly polar solvent such as acetonitrile.

It will, of course, be appreciated that all the foregoing conversions may also be effected on corresponding variables in corresponding intermediates which are not of formula (I), as appropriate under any given reaction conditions. It is, however, preferred to carry out any conversions of $R_1$ and $R_2$ at an earlier stage.

When one of $R_1$ and $R_2$ in the compound of formula (I) so obtained is an amino or an amino-containing group, the optional formation of a pharmaceutically acceptable salt thereof may be carried out in accordance with conventional procedures.

The compound of the formula (V) is generally formed in situ by the hydrolysis of a compound of the formula (VI):

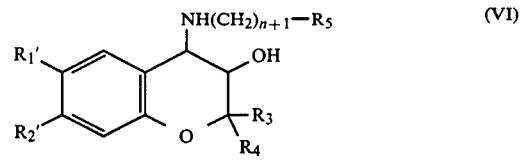

wherein $R_5$ is a group readily hydrolysable to a $-CH_2CHO$ group; and optionally thereafter converting $R_1'/R_2'$ to $R_1/R_2$.

Particularly suitable $R_5$ groups which are readily hydrolysable include those of sub-formulae (a) to (c).

wherein $R_6$ is a $C_{1-4}$ alkyl group; $R_7$ and $R_8$ are each $C_{1-4}$ alkyl groups or together represent a $-CH_2CH_2-$ or $-CH_2CH_2CH_2-$group; and $R_9$ is a $C_{1-4}$ alkyl group.

Suitable example of $R_6$, $R_7$ and $R_8$ and $R_9$ include methyl and ethyl. $R_7$ and $R_8$ may also suitably be $-CH_2CH_2-$.

Hydrolysis is generally conveniently effected under the same conditions as the foregoing cyclisation which proceeds sequentially in situ.

A compound of formula (VI) may be prepared by reacting a compound of formula (VII):

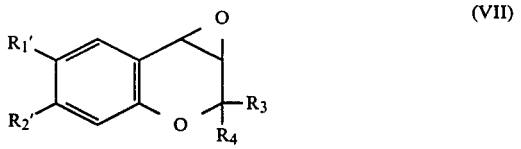

wherein $R_1'$ and $R_2'$ and $R_3$ and $R_4$ are as hereinbefore defined with a compound of formula (VIII):

wherein n and $R_5$ are as hereinbefore defined.

The reaction is normally carried out in a solvent at low, medium or high temperature. The solvent may be an alcohol, such as methanol or ethanol.

A compound of formula (VII) may be prepared, preferably in situ, by reacting a compound of formula (IX):

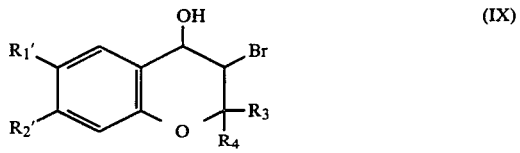

wherein $R_1'$, $R_2'$, $R_3$ and $R_4$ are as hereinbefore defined and the hydroxy group is trans to the bromo atom, with a base, such as potassium hydroxide, with ether or aqueous dioxan.

Compounds of formula (IX) are known and may be prepared in accordance with any appropriate known process, for example, by the process described in the aforementioned U.S. patents and European patent publications. Schematically, such process can be depicted thus:

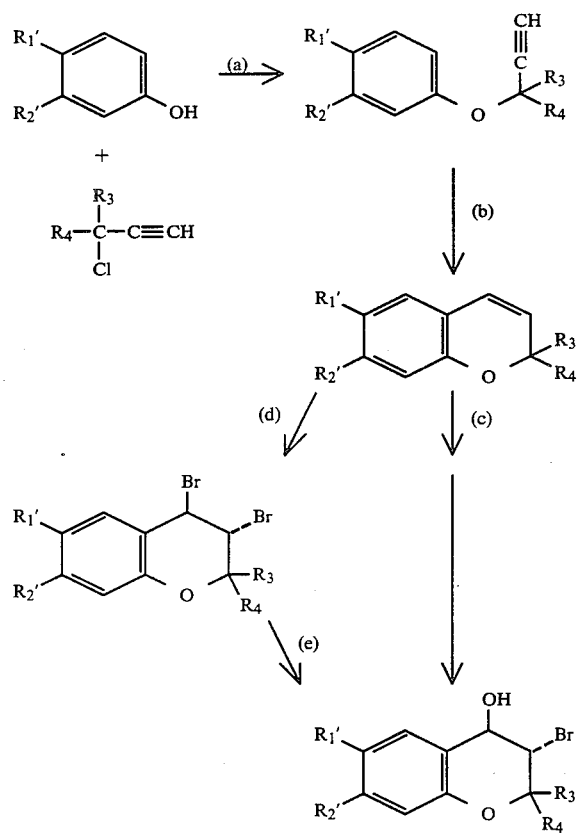

(a) Room temperature; NaOH/40% benzyltrimethylammonium hydroxide in methanol;
(b) Heat in o-dichlorobenzene;
(c) N-bromosuccinimide/dimethylsulphoxide/water;
(d) Bromine in carbon tetrachloride; and
(e) Acetone/water.

The above process may produce mixtures of compounds during reaction (b) owing to the two sites available for ring formation. In is therefore advisable to remove any of the undesired compound by, for example, chromatography, before reaction (c) or or (d).

Compounds of formula (VIII) may be prepared from the corresponding compound of formula (X).

When $R_5$ is of sub-formula (a) such preparation is carried out by enol etherification, such as described in DE-OS 2647966.3 or U.S. Pat. No. 4,180,585 and BE 866.857 or U.S. Pat. No. 4,200,645.

When $R_5$ is of sub-formula (b) apt methods of acetalation include those of DE-OS 26479663 or U.S. Pat. No. 4,180,585.

When $R_5$ is of sub-formula (c) apt methods of enol esterification include those of DE-OS 2647966.3 or U.S. Pat. No. 4,180,585.

It is preferred that the compounds of formula (I) are isolated in substantially pure form.

Compounds of the formula (I) are particularly preferably isolated as crystalline solids.

As mentioned previously, the compounds of formula (I) have been found to have blood-pressure lowering activity. They are therefore useful in the treatment of hypertension.

The present invention accordingly provides a pharmaceutical composition which comprises a compound of formula (I) and a pharmaceutically acceptable carrier. In particular, the present invention provides an anti-hypertensive pharmaceutical composition which comprises an anti-hypertensive effective amount of a compound of formula (I) and a pharmaceutically acceptable carrier.

The compositions are preferably adapted for oral administration. However, they may be adapted for other modes of administration, for example parenteral administration for patients suffering from heart failure.

In order to obtain consistency of administration it is preferred that a composition of the invention is in the form of a unit-dose. Suitable unit dose forms include tablets, capsules and powders in sachets or vials. Such unit dose forms may contain from 1 to 100 mg of a compound of the invention and more usually from 2 to 50 mg, for example 5 to 25 mg such as 6, 10, 15 or 20 mg. Such compositions may be administered from 1 to 6 times a day, more usually from 2 to 4 times a day, in a manner such that the daily dose is from 5 to 200 mg for a 70 kg human adult and more particularly from 10 to 100 mg.

The compositions of the invention may be formulated with conventional excipients, such as a filler, a disintegrating agent, a binder, a lubricant, a flavouring agent. They are formulated in conventional manner, for example in a manner similar to that used for known anti-hypertensive agents, diuretics and β-blocking agents.

The present invention further provides a compound of formula (I) for use in the treatment of hypertension.

The present invention yet further provides a method of treating hypertension in mammals including man, which comprises administering to the suffering mammal an anti-hypertensive effective amount of a compound of formula (I) or a pharmaceutical composition of the invention.

The following descriptions relate to the preparation of intermediates and the following examples relate to the preparation of a compound of formula (I).

DESCRIPTION 1

6-cyano-3,4-dihydro-2,3-dimethyl-trans-4-(4,4-diethoxybutylamino)-2H-benzo[b]pyran(D1)

6-Cyano-3,4-dihydro-2,2-dimethyl-3,4-epoxy-2H-benzo[b]pyran (200 mg) and 4-aminobutyraldehyde diethylacetal (200 ng) were heated to 100° C. for 1.5 hrs, a clear yellow solution forming during this time. After cooling, dilution with ether, and washing successively with water and brine, drying over $Na_2SO_4$ and evaporation, the aminoacetal was obtained as a pale yellow oil (291 mgr).

NMR ($CDCl_3$) δ 1.23 (t, J=7, 6H) overlapping (S, 3H), 1.45–1.96 (m, 4H) overlapping 1.53 (S, 3H), 2.47–2.87 (m, 2H), 3.29–3.94 (m, 6H), 4.54 (irreg t, J=5, 1H), 6.87 (d, J=8, 1H), 7.47 (q, J=8, 2, 1H), 7.74 (d, J=2, 1H).

IR (film): 3470, 225 cm$^{-1}$.

EXAMPLE 1

6-Cyano-3,4-dihydro-2,2-dimethyl-trans-4-(2-hydroxy-1-pyrrolidinyl)-2H-benzo[b]-pyran-3-ol (1)

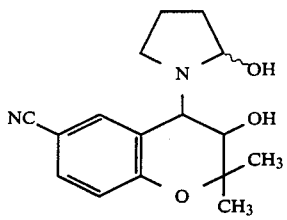

The oily acetal was dissolved in dioxan (2 ml) and treated with 2.5 MHCl (1 ml). After 30 min. the reaction was diluted with ether and neutralised with $Na_2CO_3$ solution.

The two phases were separated, the aqueous layer further extracted with ether and the combined extracts washed with water and brine and dried over $Na_2SO_4$. The organic phase was filtered and applied to Kieselgel 60 (10 g) and diluted with ethyl acetate-heptane-triethylamine (10:20:2). Three fractions were obtained (total 128 mg) containing the title compound. TLC (silica gel; ethyl acetate-heptane-triethylamine 10:20:2) showed the presence of varying amount of the two positional isomers in each fraction.

IR (KBr disc) 3450, 2230 cm$^{-1}$ for all three fractions.

Mass spectrum (Isobutane and ammonia C.I.) showed m/z 271 (MH$^+$—$H_2O$) for all three fractions.

EXAMPLE 2

6-Acetyl-3,4-dihydro-2,2-dimethyl-trans-4-(2-hydroxy-1-pyrrolidinyl)-2H-benzo[b]pyran-3-ol

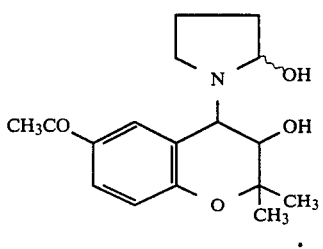

6-Acetyl-3,4-dihydro-2,2-dimethyl-trans-4-(4,4-diethoxybutylamino)-2H-benzo[b]pyran-3-ol was prepared in a similar manner to that of description 1.

NMR ($CDCl_3$) δ 1.20 (t, J=7, 6H) overlapping 1.27 (S, 3H), 1.47–1.83 (M, 4H) overlapping 1.55 (S, 3H), 2.20–2.87 (M, 4H) overlapping 2.53 (S, 3H), 3.17–3.83 (M, 6H), 4.43 (t, J=5, 1H), 6.68 (d, J=8 1H), 7.63 (q, J=8, 2, 1H), 7.87 (d, J=2, 1H).

The aminoacetal was treated in the same manner as the acetal in example 1. Extraction with diethyl ether gave 6-acetyl-3,4-dihydro-2,2-dimethyl-trans-4-(2-hydroxy-1-pyrrolidinyl)-2H-benzo[b]pyran-3-ol.

IR (KBr disc) 3420, 1675 cm$^{-1}$.

Mass spectrum (electron impact) shows M$^+$—$H_2O$ at m/z 287.1520. Calculated for $C_{17}H_{21}NO_3$ 287.1521.

PHARMACOLOGICAL DATA

Systolic blood pressures were recorded by a modification of the tail cuff method described by I M Claxton, M G Palfreyman, R H Poyser, R L Whiting, European Journal of Pharmacology, 37, 179 (1976). W+W BP recorder, model 8005, was used to display pulses. Prior to all measurements, rats were placed in a heated environment (33.5°±0.5° C.) before transfer to a restraining cage. Each determination of blood pressure was the mean of at least 6 readings. Spontaneously hypertensive rats (ages 12–18 weeks) with systolic blood pressures >170 mmHg were considered hypertensive.

| | Time Post Dose Hours | % Change in Systolic Blood Pressure | % Change in Heart Rate |
|---|---|---|---|
| Compound of Example 1 | | | |
| 6 rats | 1 | −22 ± 4 | −1 ± 4 |
| Dose 10 mg/kg po | 2 | −45 ± 7 | −4 ± 2 |
| Initial Blood Pressure 219 ± 3 mmHg | 4* 6** | −53 | −11 |
| Initial Heart Rate 493 ± 8 beats/min | 24 | −4 ± 8 | −7 ± 3 |

*At 4 hours 5 rats had no measurable pulse.
**At 6 hours 6 rats had no measurable pulse.

| | Time Post Dose Hours | % Change in Systolic Blood Pressure | % Change in Heart Rate |
|---|---|---|---|
| Compound of Example 2 | | | |
| 6 rats | 1 | −2 ± 4 | −8 ± 2 |
| Dose 10 mg/kg po | 2 | −7 ± 2 | −3 ± 1 |
| Initial Blood Pressure 219 ± 5 mm/Hg | 4 6 | −44 ± 7* ** | −2 ± 2 |
| Initial Heart Rate 511 ± 4 beats/min | 24 | 1 ± 3 | −9 ± 3 |

*At 4 hours 2 rats had no measurable pulse.
**At 6 hours all 6 rats had no measurable pulse.

TOXICITY

No toxic effects were observed in the above test.

Compounds of formula (I) wherein:
one of $R_1$ and $R_2$ is hydrogen and the other is selected from the class of alkylcarbonyl, alkoxycarbonyl, alkylcarbonyloxy, alkylhydroxymethyl, nitro, cyano, chloro, trifluoromethyl, alkylsulphinyl, alkylsulphonyl, alkoxysulphinyl, alkoxysulphonyl, alkylcarbonylamino, alkoxycarbonylamino, or aminosulphinyl, aminosulphonyl or aminocarbonyl, the amino moiety being optionally substituted by one or two alkyl groups, or alkylsulphinylamino, alkylsulphonylamino, alkoxysulphinylamino or alkoxysulphonylamino, or ethylenyl terminally substituted by alkylcarbonyl, nitro or cyano or —C(alkyl)NOH or —C(alkyl)NNH$_2$, the alkyl groups or alkyl moieties of alkyl-containing groups having from 1 to 6 carbon atoms;

one of $R_3$ and $R_4$ is hydrogen or alkyl having from 1 to 4 carbon atoms and the other is alkyl having from 1 to 4 carbon atoms, or $R_3$ and $R_4$ together with the carbon atoms to which they are attached are spiroalkyl having from 3 to 6 carbon atoms; and the azacycle and OH moieties are trans; and n is 1 or 2. may be oxidized to form a compound of formula (A)

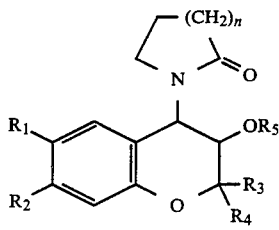

wherein $R_1$ to $R_4$ and n are as defined immediately above and $R_5$ is hydrogen. The oxidation is preferably carried out in a solvent as aqueous methanol with a metal periodate such as potassium periodate.

In the case where $R_5$ in the compound of formula (A) is to be alkyl of 1 to 3 carbon atoms or carboxylic acyl of 1 to 8 carbon atoms, the compound of formula (A), obtained from the oxidation, wherein $R_5$ is hydrogen, is alkylated or acylated with an alkylating agent of 1 to 3 carbon atoms or an acylating agent of 1 to 8 carbon atoms.

Compounds of formula (A) are claimed in U.S. Pat. No. 4,446,113, issued May 1, 1984, as anti-hypertensive agents useful in the treatment of high blood pressure. Example 3 hereof illustrates the use of a compound of formula (I) as an intermediate to make a compound of formula (A).

EXAMPLE 3

Production of 6-Cyano-3,4-dihydro-2,2-dimethyl-trans-4-(2-oxo-1-pyrrolidinyl)-2H-benzo[b]pyran-3-ol 6-Cyano-3,4-dihyro-2,2-dimethyl-trans-4-(2-hydroxy-1-pyrrolidinyl)-2H-benzo[b]pyran-3-ol (5 mg), dissolved in methanol water (1 ml) was treated with an excess of sodium periodate with stirring during 15 hours at room temperature. Evaporation of solvents and extraction by ethyl acetate gave material having identical thin layer characteristics when applied to silica gel plates developed in either chloroform-methanol (15:1) or heptane-ethyl acetate-triethylamine and infra red spectrum to the title compound reported in Example 1 of U.S. Pat. No. 4,446,113.

I claim:

1. A compound of formula (I):

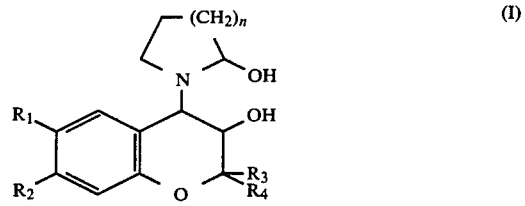

wherein:

either one of $R_1$ and $R_2$ is hydrogen and the other is selected from the class of $C_{1-6}$ alkylcarbonyl, benzoyl, $C_{1-6}$ alkoxycarbonyl, $C_{1-6}$ alkylcarbonyloxy, $C_{1-6}$ alkylhydroxymethyl, nitro, cyano, chloro, trifluoromethyl, $C_{1-6}$ alkylsulphinyl, $C_{1-6}$ alkylsulphonyl, $C_{1-6}$ alkoxysulphinyl, $C_{1-6}$ alkoxysulphonyl, $C_{1-6}$ alkylcarbonylamino, $C_{1-6}$ alkoxycarbonylamino, $C_{1-6}$ alkylthiocarbonyl, $C_{1-6}$ alkoxy-thiocarbonyl, $C_{1-6}$ alkylthiocarbonyloxy, $C_{1-6}$ alkyl-thiolmethyl, formyl or aminosulphinyl, aminosulphonyl or aminocarbonyl, the amino moiety being optionally substituted by one or two $C_{1-6}$ alkyl groups, or $C_{1-6}$ alkylsulphinylamino, $C_{1-6}$ alkylsulphonylamino $C_{1-6}$ alkoxysulphinylamino or $C_{1-6}$ alkoxysulphonylamino or ethylenyl terminally substituted by $C_{1-6}$ alkylcarbonyl, nitro or cyano, or —C($C_{1-6}$ alkyl)NOH or —C($C_{1-6}$ alkyl)NNH$_2$, or one of $R_1$ and $R_2$ is nitro, cyano or $C_{1-3}$ alkylcarbonyl and the other is methoxy or amino optionally substituted by one or two $C_{1-6}$ alkyl or by $C_{2-7}$ alkanoyl;

one of $R_3$ and $R_4$ is hydrogen or $C_{1-4}$ alkyl and the other is $C_{1-4}$ alkyl or $R_3$ and $R_4$ together are $C_{2-5}$ polymethylene;

the azacycle and OH moieties are trans; and n is 1 or 2;

or when one or other other of $R_1$ and $R_2$ is an amino or an amino-containing group, a pharmaceutically acceptable salt thereof.

2. A compound according to claim 1 wherein one of $R_1$ and $R_2$ is hydrogen and the other is selected from the class of $C_{1-6}$ alkylcarbonyl, $C_{1-6}$ alkoxycarbonyl, $C_{1-6}$ alkoxycarbonyloxy, $C_{1-6}$ alkylhydroxymethyl, nitro, cyano or chloro.

3. A compound according to claim 1, wherein one of $R_1$ and $R_2$ is hydrogen and the other is cyano or nitro.

4. 6-cyano-3,4-dihydro-2,2-dimethyl-trans-4-(2-hydroxy-1-pyrrolidinyl)-2H-benzo[b]-pyran-3-ol or 6-acetyl-3,4-dihydro-2,2-dimethyl-trans-4-(2-hydroxy-1-pyrrolidinyl)-2H-benzo[b]pyran-3-ol.

5. A compound according to claim 1, wherein one of $R_1$ and $R_2$ is hydrogen and the other is optionally substituted amino.

6. A compound according to claim 1, in substantially pure form.

7. A pharmaceutical composition for the treatment of hypertension, comprising an anti-hypertensive effective amount of a compound according to claim 1 or a pharmaceutically acceptable salt thereof and a pharmaceutically acceptable carrier.

8. A method of treatment of hypertension in mammals which comprises the administration to the sufferer of an anti-hypertensive effective amount of a compound according to claim 1 or a pharmaceutically acceptable salt thereof.

* * * * *